United States Patent [19]
Conway

[11] Patent Number: 6,140,556
[45] Date of Patent: Oct. 31, 2000

[54] SOYBEAN CULTIVAR CX414CRR

[75] Inventor: Michael P. Conway, Plainfield, Ind.

[73] Assignee: DeKalb Genetics Corporation, DeKalb, Ill.

[21] Appl. No.: 09/231,756

[22] Filed: Jan. 15, 1999

[51] Int. Cl.[7] .............................. A01H 5/00; A01H 5/10; A01H 1/02; C12N 5/04
[52] U.S. Cl. ........................ 800/312; 435/415; 800/260
[58] Field of Search .................................. 435/415, 426, 435/430; 800/260, 312

[56] References Cited

U.S. PATENT DOCUMENTS

| | | | |
|---|---|---|---|
| 5,084,082 | 1/1992 | Sebastian | 800/312 |
| 5,304,728 | 4/1994 | Eby | 800/312 |
| 5,569,815 | 10/1996 | Eby | 800/312 |
| 5,576,474 | 11/1996 | Lussenden | 800/312 |
| 5,922,931 | 7/1999 | Conway | 800/312 |
| 5,922,932 | 7/1999 | Conway | 800/312 |

OTHER PUBLICATIONS

Allard, R.W., University of California, Davis, California. "Principles of Plant Breeding," Published by John Wiley & Sons, New York, University of California, Davis, California, pp. 50–98, 1960.

Bernard, ed., "Evaluation of Maturity Groups I and II of the U.S.D.A. Soybean Collection," pp. 1–3, 58–59, Sep. 1966.

Bernard, ed., "Evaluation of Maturity Groups III and IV of the U.S.D.A. Soybean Collection," pp. 1–3, 5a–5A, 8a–8d, 9a–9d, 14a–14d, 17a–17d, 24a–24d, and 25a–25d, Apr. 1969.

Fehr, "In: Soybeans: Improvement, Production and Uses," 2nd Edition, *Manograph* 16, p. 249 and 259, 1987.

Fehr, Walter R., Iowa State University. "Principles of Cultivar Development," vol. 1 Theory and Technique and vol. 2 Crop Species, Soybean, Published by Macmillian Publishing Company, New York, pp. 360–376, 1987.

Nickell and Bernard, "Registration of L84–5873 and L84–5932 Soybean Germplasm Lines Resistant to Brown Stem Rot," *Crop. Sci.*, 32:835, 1992.

Plant Variety Protection Certification Application 9000006.

Sneep, J. and A.J.T. Hendriksen, eds., "Plant Breeding Perspectives," Wageningen: Centre for Agricultural Publishing and Documentation, 1979.

*Primary Examiner*—Elizabeth F. McElwain
*Assistant Examiner*—Ashwin Mehta
*Attorney, Agent, or Firm*—Fulbright & Jaworski

[57] ABSTRACT

The instant invention relates to the novel soybean cultivar designated CX414cRR. Provided by the invention are the seeds, plants and derivatives of the soybean cultivar CX414cRR. Also provided by the invention are tissue cultures of the soybean cultivar CX414cRR and the plants regenerated therefrom. Still further provided by the invention are methods for producing soybean plants by crossing the soybean cultivar CX414cRR with itself or another soybean variety, as well as the plants produced by such methods.

19 Claims, No Drawings

SOYBEAN CULTIVAR CX414CRR

BACKGROUND OF THE INVENTION

1. Field of the Invention

The present invention relates generally to the field of soybean breeding. In particular, the invention relates to the novel soybean cultivar CX414cRR.

2. Description of Related Art

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. These important traits may include higher seed yield, resistance to diseases and insects, better stems and roots, tolerance to drought and heat, better agronomic quality, resistance to herbicides, and improvements in compositional traits.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, recurrent selection and backcrossing.

The complexity of inheritance influences choice of the breeding method. Backcross breeding is used to transfer one or a few favorable genes for a highly heritable trait into a desirable cultivar. This approach has been used extensively for breeding disease-resistant cultivars (Bowers et al., 1992; Nickell and Bernard, 1992). Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for generally three or more years. The best lines are candidates for new commercial cultivars. Those still deficient in a few traits may be used as parents to produce new populations for further selection.

These processes, which lead to the final step of marketing and distribution, may take as much as eight to 12 years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to one or more widely grown standard cultivars. Single observations are generally inconclusive, while replicated observations provide a better estimate of genetic worth.

The goal of plant breeding is to develop new, unique and superior soybean cultivars and hybrids. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line de novo, or even very similar lines, having the same soybean traits.

Each year, the plant breeder selects the germplasm to advance to the next generation. This germplasm is grown under unique and different geographical, climatic and soil conditions, and further selections are then made, during and at the end of the growing season. The cultivars which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same cultivar twice by using the exact same original parents and the same selection techniques. This unpredictability results in the expenditure of large amounts of research monies to develop superior new soybean cultivars.

The development of new soybean cultivars requires the development and selection of soybean varieties, the crossing of these varieties and selection of progeny from the superior hybrid crosses. The hybrid seed is produced by manual crosses between selected male-fertile parents or by using male sterility systems. Hybrids may be identified by using certain single locus traits such as pod color, flower color, pubescence color or herbicide resistance which indicate that the seed is truly a hybrid. Additional data on parental lines as well as the phenotype of the hybrid influence the breeder's decision whether to continue with the specific hybrid cross.

Pedigree breeding and recurrent selection breeding methods are used to develop cultivars from breeding populations. Breeding programs combine desirable traits from two or more cultivars or various broad-based sources into breeding pools from which cultivars are developed by selfing and selection of desired phenotypes. The new cultivars are evaluated to determine which have commercial potential.

Pedigree breeding is commonly used for the improvement of self-pollinating crops. Two parents which possess favorable, complementary traits are crossed to produce an $F_1$. An $F_2$ population is produced by selfing one or several $F_1$'s. Selection of the best individuals may begin in the $F_2$ population (or later depending upon the breeders objectives); then, beginning in the $F_3$, the best individuals in the best families can be selected. Replicated testing of families can begin in the $F_3$ or $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self-or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genetic loci for simply inherited, highly heritable traits into a desirable homozygous cultivar which is the recurrent parent. The source of the trait to be transferred is called the donor or nonrecurrent parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, soybean breeders commonly harvest one or more pods from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh pods with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

Descriptions of other breeding methods that are commonly used for different traits and crops can be found in one of several reference books (e.g., Allard, 1960; Simmonds, 1979; Sneep et al., 1979; Fehr, 1987a,b).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Soybean, *Glycine max* (L), is an important and valuable field crop. Thus, a continuing goal of plant breeders is to develop stable, high yielding soybean cultivars that are agronomically sound. The reasons for this goal are to maximize the amount of grain produced on the land used and to supply food for both animals and humans. To accomplish this goal, the soybean breeder must select and develop soybean plants that have the traits that result in superior cultivars.

SUMMARY OF THE INVENTION

One aspect of the present invention relates to seed of the soybean cultivar designated CX414cRR. The invention also relates to plants produced by growing the seed of the soybean cultivar CX414cRR, as well as the derivatives of such plants. As used herein, the term "plant" includes plant cells, plant protoplasts, plant cells of a tissue culture from which soybean plants can be regenerated, plant calli, plant clumps, and plant cells that are intact in plants or parts of plants, such as pollen, flowers, seeds, pods, leaves, stems, and the like.

Another aspect of the invention relates to a tissue culture of regenerable cells of the soybean cultivar CX414cRR, as well as plants regenerated therefrom, wherein the regenerated soybean plant is capable of expressing all the physiological and morphological characteristics of a plant grown from the soybean seed designated CX414cRR.

Yet another aspect of the current invention is a soybean plant comprising a single locus conversion of the soybean cultivar CX414cRR, wherein the soybean plant is otherwise capable of expressing all the physiological and morphological characteristics of the soybean cultivar CX414cRR. In particular embodiments of the invention, the single locus conversion may comprise a transgenic gene which has been introduced by genetic transformation into the soybean cultivar CX414cRR or a progenitor thereof. In still other embodiments of the invention, the single locus conversion may comprise a dominant or recessive allele. The locus conversion may confer potentially any trait upon the single locus converted plant, including herbicide resistance, insect resistance, resistance to bacterial, fungal, or viral disease, male fertility or sterility, and improved nutritional quality.

Still yet another aspect of the invention relates to a first generation ($F_1$) hybrid soybean seed produced by crossing a plant of the soybean cultivar CX414cRR to a second soybean plant. Also included in the invention are the $F_1$ hybrid soybean plants grown from the hybrid seed produced by crossing the soybean cultivar CX414cRR to a second soybean plant. Still further included in the invention are the seeds of an $F_1$ hybrid plant produced with the soybean cultivar CX414cRR as one parent, the second generation ($F_2$) hybrid soybean plant grown from the seed of the $F_1$ hybrid plant, and the seeds of the $F_2$ hybrid plant.

Still yet another aspect of the invention is a method of producing soybean seeds comprising crossing a plant of the soybean cultivar CX414cRR to any second soybean plant, including itself or another plant of the cultivar CX414cRR. In particular embodiments of the invention, the method of crossing comprises the steps of a) planting seeds of the soybean cultivar CX414cRR; b) cultivating soybean plants resulting from said seeds until said plants bear flowers; c) allowing fertilization of the flowers of said plants; and, d) harvesting seeds produced from said plants.

Still yet another aspect of the invention is a method of producing hybrid soybean seeds comprising crossing the soybean cultivar CX414cRR to a second, distinct soybean plant which is nonisogenic to the soybean cultivar CX414cRR. In particular embodiments of the invention, the crossing comprises the steps of a) planting seeds of soybean cultivar CX414cRR and a second, distinct soybean plant, b) cultivating the soybean plants grown from the seeds until the plants bear flowers; c) cross pollinating a flower on one of the two plants with the pollen of the other plant, and d) harvesting the seeds resulting from the cross pollinating.

DETAILED DESCRIPTION OF THE INVENTION

The instant invention provides methods and composition relating to plants, seeds and derivatives of the soybean cultivar CX414cRR. Soybean cultivar CX414cRR has superior characteristics and is derived from a bulk of sixteen F3 plant selections from the cross Asgrow 4138×[CX445 (CX411×CX415-40-3)]. The origin and breeding history of CX414cRR were as follows

| | |
|---|---|
| Fall 1992 | The cross CX415 × A5403-40-3-2 was made. A5403 is an Asgrow variety that has had a gene inserted via transformation that confers resistance to the herbicide glyphosate. |
| Winter 1993 | Monsanto made BC1. |
| Summer 1993 | Monsanto made BC2. |
| Winter 1994 | CX411 was crossed with BC2 of CX415 × 40-3-2. |
| Summer 1994 | Modified BC3F1 generation was grown. CX445 was crossed with Modified BC3 of CX411 × CX415-40-3-2. |
| Winter 1995 | Modified BC4F1 and BC4F2 generations were grown. |
| Summer 1995 | Modified BC4F3 generation was grown. Asgrow 4138 was crossed with Modified BC4F3 of [CX445 (CX411 × CX415-40-3)]. |
| Winter 1996 | The F1 and F2 generations were grown. |
| Summer 1996 | The F3 generation was grown. |
| Winter 1997 | The F4 and F5 seed were grown. |
| Summer 1997 | F6 seed was grown. |
| Winter 1998 | F7 and F8 seed were grown. |
| Summer 1998 | F9 seed was grown. |
| November 1998 | The variety was commercialized as CX414cRR. |

| | |
|---|---|
| SEED SHAPE: | Spherical |
| SEED COAT COLOR (Mature Seed): | Yellow |
| SEED COAT LUSTER (Mature Hand Shelled Seed): | Dull |
| SEED SIZE (Mature Seed): | 16.8 g/100 seeds |
| HILUM COLOR: (Mature Seed) | Black |
| COTYLEDON COLOR (Mature Seed): | Yellow |
| SEED PROTEIN PEROXIDASE ACTIVITY: | 90% High 10% Low |
| SEED PROTEIN ELECTROPHORECTIC BAND: | — |
| HYPOCOTYL COLOR: | Green with Bronze Band |
| LEAFLET SHAPE: | Ovate |
| LEAFLET SIZE: | Medium |
| LEAF COLOR: | Medium Green |
| FLOWER COLOR: | White |
| POD COLOR: | Tan |
| PLANT PUBESCENCE COLOR: | Tawny |
| PLANT TYPE: | Bushy |
| PLANT HABIT: | Indeterminate |
| MATURITY GROUP: | IV |
| DISEASE REACTION: (0 = NOT TESTED; 1 = SUSCEPTIBLE; 2 = RESISTANT) | |
| BACTERIAL DISEASES | FUNGAL DISEASES |
| Bacterial Pustule: 0 | Brown Spot: 0 |
| Bacterial Blight: 0 | Frogeye Leaf Spot: 0 |
| Wildfire: 0 | Target Spot: 0 |

-continued

| | | | |
|---|---|---|---|
| VIRAL DISEASES | | Downy Mildew: | 0 |
| Bud Blight: | 0 | Powdery Mildew: | 0 |
| Yellow Mosaic: | 0 | Brown Stem Rot: | 0 |
| Cowpea Mosaic: | 0 | Stem Canker: | 0 |
| Pod Mottle: | 0 | Pod and Stem Blight: | 0 |
| Seed Mottle: | 0 | Purple Seed Stain: | 0 |
| NEMATODE DISEASES | | Rhizoctonia Root Rot: | 0 |
| Soybean Cyst Nematode: | 2* (Race 3) | Sclerotinia White Mold: | 0 |
| Lance Nematode: | 0 | Sudden Death Syndrome: | 0 |
| Southern Root Knot Nematode: | 0 | Phytophthora Rot: | 1 |
| Northern Root Knot Nematode: | 0 | Race(s): | |
| | | Race 1: | 0 |
| Peanut Root Knot Nematode: | 0 | Race 2: | 0 |
| | | Race 3: | 0 |
| Reniform Nematode: | 0 | Race 4: | 0 |
| | | Race 5–9: | 0 |
| PHYSIOLOGICAL RESPONSES: (0 = NOT TESTED; 1 = SUSCEPTIBLE; 2 = RESISTANT) | | | |
| Iron Chlorosis on Calcareous Soil: | 0 | | |
| Other: | 0 | | |
| INSECT REACTION: (0 = NOT TESTED; 1 = SUSCEPTIBLE; 2 = RESISTANT) | | | |
| Mexican Bean Beetle: | 0 | | |
| Potato Leaf Hopper: | 0 | | |
| Other: | 0 | | |

*Moderately resistant

Soybean variety CX414cRR has been judged to be uniform for breeding purposes and testing after three generations of selfing. CX414cRR was reproduced and judged uniform and stable for an additional six generations. Cultivar CX414cRR shows no variants other than what would normally be expected due to environment or that would occur for almost any characteristic during the course of repeated sexual reproduction. Some of the criteria used to select in various generations include: seed yield, lodging resistance, emergence, seedling vigor, disease tolerance, maturity, plant height and shattering resistance.

The inventor believes that CX414cRR is most similar to soybean variety CX445. However, CX414cRR differs from this cultivar in at least the following traits: CX414cRR has tan pods and is resistant to glyphosate whereas, CX445 has brown pods and is susceptible to glyphosate.

I. Variety Comparison

Direct comparisons were made between CX414cRR and a competing commercial variety. Traits measured included yield, maturity, moisture, lodging, plant height, field emergence, and seedling vigor. The results of the comparison are presented in below. Shown are the number of tests in which the varieties were compared, the deviation or difference of the results, the test means, and the traits which showed a significant difference and the significance level.

| VARIETIES COMPARED | TYP | SEL % M | YLD B/A | MAT DAY | MST % | LDG RAT | PLTH IN | FDEMR RAT | SDVG RAT |
|---|---|---|---|---|---|---|---|---|---|
| VARIETY COMPARISON CX414cRR | | | | | | | | | |
| CX414cRR | R 17 | 97.9 | 43.8 | 277.5 | 11.9 | 3.9 | 39.5 | 3.1 | 2.5 |
| CX445 | | 101.2 | 47.2 | 278.5 | 11.4 | 3.9 | 42.5 | 2.8 | 2.5 |
| Deviation | | −3.3 | −3.4 | −1.0 | 0.4 | 0.0 | −3.0 | 0.4 | 0.0 |
| TestMean | | 100.0 | 46.6 | 277.6 | 11.6 | 2.9 | 39.8 | 2.8 | 2.5 |
| Sig | | ** | ** | | + | | | | |

Significance levels are indicated as: + = 10%, * = 5%, ** = 1%
TYP = Research - No. of tests
SEL % M = Selection Index (% test mean)
YLD B/A = Yield (bushels/acre)
MAT DAY = Maturity (days)
MST % = Moisture (percentage)
LDG RAT = Lodging Rating (scale: 1–9, 1 = best)
PLTHT IN = Plant Height (inches)
FDEMR RAT = Field Emergence Rating (scale: 1–9, 1 = best)
SDVG RAT = Seedling Vigor Rating (scale: 1–9, 1 = best)

II. Breeding Soybean Cultivar CX414cRR

An important aspect of the invention concerns methods for crossing the soybean cultivar CX414cRR with itself or a second plant and the seeds and plants produced by such methods. These methods can be used for propagation of the soybean cultivar CX414cRR, or can be used to produce hybrid soybean seeds and the plants grown therefrom. Hybrid soybean plants can be used by farmers in the commercial production of soy products or may be advanced in certain breeding protocols for the production of novel soybean cultivars. The cultivar of the present invention is well suited to the development of new cultivars because of the elite nature of it's genetic background. A hybrid plant can also be used as a recurrent parent at any given stage in a backcrossing protocol during the production of a single locus conversion of the soybean cultivar CX414cRR.

In selecting a second plant to cross with CX414cRR for the purpose of developing novel soybean cultivars, it will typically be desired to choose those plants which either themselves exhibit one or more selected desirable characteristics or which exhibit the desired characteristic(s) when in hybrid combination. Examples of potentially desired characteristics include seed yield, lodging resistance, emergence, seedling vigor, disease tolerance, maturity, plant height and shattering resistance.

Any time the soybean cultivar CX414cRR is crossed with another, different, cultivar, first generation ($F_1$) soybean progeny are produced. The hybrid progeny are produced regardless of characteristics of the two cultivars produced. As such, an $F_1$ hybrid soybean plant may be produced by crossing CX414cRR with any second soybean plant. The second soybean plant may be genetically homogeneous (e.g., inbred) or may itself be a hybrid. Therefore, any $F_1$ hybrid soybean plant produced by crossing soybean cultivar CX414cRR with a second soybean plant is a part of the present invention.

Soybean plants (Glycine max L.) can be crossed by either natural or mechanical techniques (see, e.g., Fehr, 1980). Natural pollination occurs in soybeans either by self pollination or natural cross pollination, which typically is aided by pollinating organisms. In either natural or artificial crosses, flowering and flowering time are an important consideration. Soybean is a short-day plant, but there is considerable genetic variation for sensitivity to photoperiod (Hamner, 1969; Criswell and Hume, 1972). The critical day length for flowering ranges from about 13 h for genotypes adapted to tropical latitudes to 24 h for photoperiod-insensitive genotypes grown at higher latitudes (Shibles et al., 1975). Soybeans seem to be insensitive to day length for 9 days after emergence. Photoperiods shorter than the critical day length are required for 7 to 26 days to complete flower induction (Borthwick and Parker, 1938; Shanmugasundaram and Tsou, 1978).

Sensitivity to day length is an important consideration when genotypes are grown outside of their area of adaptation. When genotypes adapted to tropical latitudes are grown in the field at higher latitudes, they may not mature before frost occurs. Plants can be induced to flower and mature earlier by creating artificially short days or by grafting (Fehr, 1980). Soybeans frequently are grown in winter nurseries located at sea level in tropical latitudes where day lengths are much shorter than their critical photoperiod. The short day lengths and warm temperatures encourage early flowering and seed maturation, and genotypes can produce a seed crop in 90 days or fewer after planting. Early flowering is useful for generation advance when only a few self-pollinated seeds per plant are needed, but not for artificial hybridization because the flowers self-pollinate before they are large enough to manipulate for hybridization. Artificial lighting can be used to extend the natural day length to about 14.5 h to obtain flowers suitable for hybridization and to increase yields of self-pollinated seed.

The effect of a short photoperiod on flowering and seed yield can be partly offset by altitude, probably due to the effects of cool temperature (Major et al., 1975). At tropical latitudes, cultivars adapted to the northern U.S. perform more like those adapted to the southern U.S. at high altitudes than they do at sea level.

The light level required to delay flowering is dependent on the quality of light emitted from the source and the genotype being grown. Blue light with a wavelength of about 480 nm requires more than 30 times the energy to inhibit flowering as red light with a wavelength of about 640 nm (Parker et al., 1946).

Temperature can also play a significant role in the flowering and development of soybean (Major et al., 1975). It can influence the time of flowering and suitability of flowers for hybridization. Temperatures below 21° C. or above 32° C. can reduce floral initiation or seed set (Hamner, 1969; van Schaik and Probst, 1958). Artificial hybridization is most successful between 26° C. and 32° C. because cooler temperatures reduce pollen shed and result in flowers that self-pollinate before they are large enough to manipulate. Warmer temperatures frequently are associated with increased flower abortion caused by moisture stress; however, successful crosses are possible at about 35° C. if soil moisture is adequate.

Soybeans have been classified as indeterminate, semi-determinate, and determinate based on the abruptness of stem termination after flowering begins (Bernard and Weiss, 1973). When grown at their latitude of adaptation, indeterminate genotypes flower when about one-half of the nodes on the main stem have developed. They have short racemes with few flowers, and their terminal node has only a few flowers. Semi-determinate genotypes also flower when about one-half of the nodes on the main stem have developed, but node development and flowering on the main stem stops more abruptly than on indeterminates. Their racemes are short and have few flowers, except for the terminal one, which may have several times more flowers than those lower on the plant. Determinate cultivars begin flowering when all or most of the nodes on the main stem have developed. They usually have elongated racemes that may be several centimeters in length and may have a large number of flowers. Stem termination and flowering habit are reported to be controlled by two major genes (Bernard and Weiss, 1973).

Soybean flowers typically are self-pollinated on the day the corolla opens. The amount of natural crossing, which is typically associated with insect vectors such as honeybees, is approximately 1% for adjacent plants within a row and 0.5% between plants in adjacent rows. The structure of soybean flowers is similar to that of other legume species and consists of a calyx with five sepals, a corolla with five petals, 10 stamens, and a pistil (Carlson, 1973). The calyx encloses the corolla until the day before anthesis. The corolla emerges and unfolds to expose a standard, two wing petals, and two keel petals. An open flower is about 7 mm long from the base of the calyx to the tip of the standard and 6 mm wide across the standard. The pistil consists of a single ovary that contains one to five ovules, a style that curves toward the standard, and a club-shaped stigma. The stigma is receptive to pollen about 1 day before anthesis and remains receptive for 2 days after anthesis, if the flower petals are not removed. Filaments of nine stamens are fused, and the one nearest the standard is free. The stamens form a ring below the stigma until about 1 day before anthesis, then their filaments begin to elongate rapidly and elevate the anthers around the stigma. The anthers dehisce on the day of anthesis, pollen grains fall on the stigma, and within 10 h the pollen tubes reach the ovary and fertilization is completed (Johnson and Bernard, 1963).

Self-pollination occurs naturally in soybean with no manipulation of the flowers. For the crossing of two soybean plants, it is typically preferable, although not required, to utilize artificial hybridization. In artificial hybridization, the flower used as a female in a cross is manually cross pollinated prior to maturation of pollen from the flower, thereby preventing self fertilization, or alternatively, the male parts of the flower are emasculated using a technique known in the art. Techniques for emasculating the male parts of a soybean flower include, for example, physical removal of the male parts, use of a genetic factor conferring male sterility, and application of a chemical gametocide to the male parts.

For artificial hybridization employing emasculation, flowers that are expected to open the following day are selected on the female parent. The buds are swollen and the corolla is just visible through the calyx or has begun to emerge. Usually no more than two buds on a parent plant are prepared, and all self-pollinated flowers or immature buds are removed with forceps. Special care is required to remove immature buds that are hidden under the stipules at the leaf axil, and could develop into flowers at a later date. The flower is grasped between the thumb and index finger and the location of the stigma determined by examining the sepals. A long, curvy sepal covers the keel, and the stigma is on the opposite side of the flower. The calyx is removed by grasping a sepal with the forceps, pulling it down and around the flower, and repeating the procedure until the five sepals are removed. The exposed corolla is removed by grasping it just above the calyx scar, then lifting and wiggling the forceps simultaneously. Care is taken to grasp the corolla low enough to remove the keel petals without injuring the stigma. The ring of anthers is visible after the corolla is removed, unless the anthers were removed with the petals. Cross-pollination can then be carried out using, for example, petri dishes or envelopes in which male flowers have been collected. Desiccators containing calcium chloride crystals are used in some environments to dry male flowers to obtain adequate pollen shed.

It has been demonstrated that emasculation is unnecessary to prevent self-pollination (Walker et al., 1979). When emasculation is not used, the anthers near the stigma frequently are removed to make it clearly visible for pollination. The female flower usually is hand-pollinated immediately after it is prepared; although a delay of several hours does not seem to reduce seed set. Pollen shed typically begins in the morning and may end when temperatures are above 30° C., or may begin later and continue throughout much of the day with more moderate temperatures.

Pollen is available from a flower with a recently opened corolla, but the degree of corolla opening associated with pollen shed may vary during the day. In many environments, it is possible to collect male flowers and use them immediately without storage. In the southern U.S. and other humid climates, pollen shed occurs in the morning when female flowers are more immature and difficult to manipulate than in the afternoon, and the flowers may be damp from heavy dew. In those circumstances, male flowers are collected into envelopes or petri dishes in the morning and the open container is typically placed in a desiccator for about 4 h at a temperature of about 25° C. The desiccator may be taken to the field in the afternoon and kept in the shade to prevent excessive temperatures from developing within it. Pollen viability can be maintained in flowers for up to 2 days when stored at about 5° C. In a desiccator at 3° C., flowers can be stored successfully for several weeks; however, cultivars may differ in the percentage of pollen that germinates after long-term storage (Kuehl, 1961).

Either with or without emasculation of the female flower, hand pollination can be carried out by removing the stamens and pistil with a forceps from a flower of the male parent and gently brushing the anthers against the stigma of the female flower. Access to the stamens can be achieved by removing the front sepal and keel petals, or piercing the keel with closed forceps and allowing them to open to push the petals away. Brushing the anthers on the stigma causes them to rupture, and the highest percentage of successful crosses is obtained when pollen is clearly visible on the stigma. Pollen shed can be checked by tapping the anthers before brushing the stigma. Several male flowers may have to be used to obtain suitable pollen shed when conditions are unfavorable, or the same male may be used to pollinate several flowers with good pollen shed.

When male flowers do not have to be collected and dried in a desiccator, it may be desired to plant the parents of a cross adjacent to each other. Plants usually are grown in rows 65 to 100 cm apart to facilitate movement of personnel within the field nursery. Yield of self-pollinated seed from an individual plant may range from a few seeds to more than 1,000 as a function of plant density. A density of 30 plants/m of row can be used when 30 or fewer seeds per plant is adequate, 10 plants/m can be used to obtain about 100 seeds/plant, and 3 plants/m usually results in maximum seed production per plant. Densities of 12 plants/m or less commonly are used for artificial hybridization.

Multiple planting dates about 7 to 14 days apart usually are used to match parents of different flowering dates. When differences in flowering dates are extreme between parents, flowering of the later parent can be hastened by creating an artificially short day or flowering of the earlier parent can be delayed by use of artificially long days or delayed planting. For example, crosses with genotypes adapted to the southern U.S. are made in northern U.S. locations by covering the late genotype with a box, large can, or similar container to create an artificially short photoperiod of about 12 h for about 15 days beginning when there are three nodes with trifoliate leaves on the main stem. Plants induced to flower early tend to have flowers that self-pollinate when they are small and can be difficult to prepare for hybridization.

Grafting can be used to hasten the flowering of late flowering genotypes. A scion from a late genotype grafted on a stock that has begun to flower will begin to bloom up to 42 days earlier than normal (Kiihl et al., 1977). First flowers on the scion appear from 21 to 50 days after the graft.

Genetic male sterility is available in soybeans and may be useful to facilitate hybridization in the context of the current invention, particularly for recurrent selection programs (Brim and Stuber, 1973). The distance required for complete isolation of a crossing block is not clear; however, outcrossing is less than 0.5% when male-sterile plants are 12 m or more from a foreign pollen source (Boerma and Moradshahi, 1975). Plants on the boundaries of a crossing block probably sustain the most outcrossing with foreign pollen and can be eliminated at harvest to minimize contamination.

Cross-pollination is more common within rows than between adjacent rows; therefore, it may be preferable to grow populations with genetic male sterility on a square grid to create rows in all directions. For example, single-plant hills on 50-cm centers may be used, with subdivision of the area into blocks of an equal number of hills for harvest from bulks of an equal amount of seed from male-sterile plants in each block to enhance random pollination.

Observing pod development 7 days after pollination generally is adequate to identify a successful cross. Abortion of pods and seeds can occur several weeks after pollination, but the percentage of abortion usually is low if plant stress is minimized (Shibles et al., 1975). Pods that develop from artificial hybridization can be distinguished from self-pollinated pods by the presence of the calyx scar, caused by removal of the sepals. The sepals begin to fall off as the pods mature; therefore, harvest should be completed at or immediately before the time the pods reach their mature color. Harvesting pods early also avoids any loss by shattering.

Once harvested, pods are typically air-dried at not more than 38° C. until the seeds contain 13% moisture or less, then the seeds are removed by hand. Seed can be stored satisfactorily at about 25° C. for up to a year if relative humidity is 50% or less. In humid climates, germination percentage declines rapidly unless the seed is dried to 7% moisture and stored in an air-tight container at room temperature. Long-term storage in any climate is best accomplished by drying seed to 7% moisture and storing it at 10° C. or less in a room maintained at 50% relative humidity or in an air-tight container.

III. Single Locus Conversions

When the term soybean cultivar CX414cRR is used in the context of the present invention, this also includes any single locus conversions of that cultivar. The term single locus converted plant as used herein refers to those soybean plants which are developed by a plant breeding technique called backcrossing, wherein essentially all of the desired morphological and physiological characteristics of a cultivar are recovered in addition to the single locus transferred into the cultivar via the backcrossing technique. Backcrossing methods can be used with the present invention to improve or introduce a characteristic into the present cultivar. The term backcrossing as used herein refers to the repeated crossing of a hybrid progeny back to one of the parental soybean plants for that hybrid. The parental soybean plant which contributes the locus for the desired characteristic is termed the nonrecurrent or donor parent. This terminology refers to the fact that the nonrecurrent parent is used one time in the backcross protocol and therefore does not recur. The parental soybean plant to which the locus or loci from the nonrecurrent parent are transferred is known as the recurrent parent as it is used for several rounds in the backcrossing protocol (Poehlman et al., 1995; Fehr, 1987a,b; Sprague and Dudley, 1988).

In a typical backcross protocol, the original cultivar of interest (recurrent parent) is crossed to a second cultivar (nonrecurrent parent) that carries the single locus of interest to be transferred. The resulting progeny from this cross are then crossed again to the recurrent parent and the process is repeated until a soybean plant is obtained wherein essentially all of the desired morphological and physiological characteristics of the recurrent parent are recovered in the converted plant, in addition to the single transferred locus from the nonrecurrent parent.

The selection of a suitable recurrent parent is an important step for a successful backcrossing procedure. The goal of a backcross protocol is to alter or substitute a single trait or characteristic in the original cultivar. To accomplish this, a single locus of the recurrent cultivar is modified or substituted with the desired locus from the nonrecurrent parent, while retaining essentially all of the rest of the desired genetic, and therefore the desired physiological and morphological constitution of the original cultivar. The choice of the particular nonrecurrent parent will depend on the purpose of the backcross; one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Soybean cultivars can also be developed from more than two parents (Fehr, 1987a). The technique, known as modified backcrossing, uses different recurrent parents during the backcrossing. Modified backcrossing may be used to replace the original recurrent parent with a cultivar having certain more desirable characteristics or multiple parents may be used to obtain different desirable characteristics from each.

Many single locus traits have been identified that are not regularly selected for in the development of a new inbred but that can be improved by backcrossing techniques. Single locus traits may or may not be transgenic; examples of these traits include, but are not limited to, male sterility, herbicide resistance, resistance to bacterial, fungal, or viral disease, insect resistance, restoration of male fertility, enhanced nutritional quality, yield stability, and yield enhancement. These comprise genes generally inherited through the nucleus.

Direct selection may be applied where the single locus acts as a dominant trait. An example of a dominant trait is the herbicide resistance trait. For this selection process, the progeny of the initial cross are sprayed with the herbicide prior to the backcrossing. The spraying eliminates any plants which do not have the desired herbicide resistance characteristic, and only those plants which have the herbicide resistance gene are used in the subsequent backcross. This process is then repeated for all additional backcross generations.

One type of single locus trait having particular utility is a gene which confers resistance to the herbicide glyphosate. Glyphosate inhibits the action of the enzyme EPSPS, which is active in the biosynthetic pathway of aromatic amino acids. Inhibition of this enzyme leads to starvation for the amino acids phenylalanine, tyrosine, and tryptophan and secondary metabolites derived therefrom. Mutants of this enzyme are available which are resistant to glyphosate. For example, U.S. Pat. No. 4,535,060 describes the isolation of EPSPS mutations which confer glyphosate resistance upon organisms having the *Salmonella typhimurium* gene for EPSPS, termed aroA. A mutant EPSPS gene having similar mutations also has been cloned from *Zea mays*. The mutant gene encodes a protein with amino acid changes at residues 102 and 106. When these or other similar genes are introduced into a plant by genetic transformation, a herbicide resistant phenotype results.

Plants having inherited a transgene comprising a mutated EPSPS gene, such as the cultivar CX414cRR, may therefore, be directly treated with the herbicide glyphosate without the result of significant damage to the plant. This phenotype provides farmers with the benefit of controlling weed growth in a field of plants having the herbicide resistance trait by application of the broad spectrum herbicide glyphosate. For example, one could apply the herbicide ROUNDUP™, a commercial formulation of glyphosate manufactured and sold by the Monsanto Company, over the top in fields where the glyphosate resistant soybeans are grown. The herbicide application rates may range from about 4 ounces of ROUNDUP™ to about 256 ounces ROUNDUP™ per acre. More preferably, about 16 ounces to about 64 ounces per acre of ROUNDUP™ may be applied to the field. However, the application rate may be increased or decreased as needed, based on the abundance and/or type of weeds being treated. Additionally, depending on the location of the field and weather conditions, which will influence weed growth and the type of weed infestation, it may be desirable to conduct further glyphosate treatments. The second glyphosate application will also typically comprise an application of about 16 ounces to about 64 ounces of ROUNDUP™ per acre treated. Again, the treatment rate may be adjusted based on field conditions. Such methods of application of herbicides to agricultural crops are well known in the art and are summarized in general in Anderson, 1983.

It will be understood to those of skill in the art that a herbicide resistance gene locus may be used for direct selection of plants having the resistance gene. For example, by applying about 16 to 64 ounces of ROUNDUP™ per acre to a collection of soybean plants which either have or lack the herbicide resistance trait, the plants lacking the trait will be killed or damaged. In this way, the herbicide resistant plants may be selected and used for commercial applications or advanced in certain breeding protocols. This application may find particular use during the breeding and development of herbicide resistant elite soybean cultivars.

White flower color is an example of a recessive single locus trait. In this example, the progeny resulting from the first backcross generation ($BC_1$) are grown and selfed. The selfed progeny from the $BC_1$ plant are grown to determine which $BC_1$ plants carry the recessive gene for white flower color. In other recessive traits, additional progeny testing, for example growing additional generations such as the $BC_1F_2$, may be required to determine which plants carry the recessive gene.

Selection of soybean plants for breeding is not necessarily dependent on the phenotype of a plant and instead can be based on genetic investigations. For example, one may utilize a suitable genetic marker which is closely genetically linked to a trait of interest. One of these markers may therefore be used to identify the presence or absence of a trait in the offspring of a particular cross, and hence may be used in selection of progeny for continued breeding. This technique may commonly be referred to as marker assisted selection. Any other type of genetic marker or other assay which is able to identify the relative presence or absence of a trait of interest in a plant may also be useful for breeding purposes. Exemplary procedures for marker assisted selection which are applicable to the breeding of soybeans are disclosed in U.S. Pat. No. 5,437,697, and U.S. Pat. No. 5,491,081, both of which disclosures are specifically incorporated herein by reference in their entirety. Such methods will be of particular utility in the case of recessive traits and variable phenotypes, or where conventional assays are expensive, time consuming or otherwise disadvantageous. Types of genetic markers which could be used in accordance with the invention include, for example, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

Many qualitative characters also have potential use as phenotype-based genetic markers in soybeans; however, some or many may not differ among cultivars commonly used as parents (Bernard and Weiss, 1973). The most widely used genetic markers are flower color (purple dominant to white), pubescence color (brown dominant to gray), and pod color (brown dominant to tan). The association of purple hypocotyl color with purple flowers and green hypocotyl color with white flowers is commonly used to identify hybrids in the seedling stage. Differences in maturity, height, hilum color, and pest resistance between parents can also be used to verify hybrid plants.

IV. Origin and Breeding History of an Exemplary Single Locus Converted Plant

The soybean cultivar known as Williams '82 [*Glycine max* L. Merr.] (Reg. No. 222, PI 518671) was developed using backcrossing techniques to transfer a locus comprising the $Rps_1$ gene to the cultivar Williams (Bernard and Cremeens, 1988). Williams '82 is a composite of four resistant lines from the $BC_6F_3$ generation, which were selected from 12 field-tested resistant lines from Williams x Kingwa. The cultivar Williams was used as the recurrent parent in the backcross and the cultivar Kingwa was used as the source of the $Rps_1$ locus. This gene locus confers resistance to 19 of the 24 races of the fungal agent phytopthora rot.

The $F_1$ or $F_2$ seedlings from each backcross round were tested for resistance to the fungus by hypocotyl inoculation using the inoculum of race 5. The final generation was tested using inoculum of races 1 to 9. In a backcross such as this, where the desired characteristic being transferred to the recurrent parent is controlled by a major gene which can be readily evaluated during the backcrossing, it is common to conduct enough backcrosses to avoid testing individual progeny for specific traits such as yield in extensive replicated tests. In general, four or more backcrosses are used when there is no evaluation of the progeny for specific traits, such as yield. As in this example, lines with the phenotype of the recurrent parent may be composited without the usual replicated tests for traits such as yield, protein or oil percentage in the individual lines.

The cultivar Williams '82 is comparable to the recurrent parent cultivar Williams in all traits except resistance to phytopthora rot. For example, both cultivars have a relative maturity of 38, indeterminate stems, white flowers, brown pubescence, tan pods at maturity and shiny yellow seeds with black to light black hila.

V. Tissue Cultures and in vitro Regeneration of Soybean Plants

A further aspect of the invention relates to tissue cultures of the soybean cultivar designated CX414cRR. As used herein, the term "tissue culture" indicates a composition comprising isolated cells of the same or a different type or a collection of such cells organized into parts of a plant. Exemplary types of tissue cultures are protoplasts, calli and plant cells that are intact in plants or parts of plants, such as embryos, pollen, flowers, leaves, roots, root tips, anthers, and the like. In a preferred embodiment, the tissue culture comprises embryos, protoplasts, meristematic cells, pollen, leaves or anthers.

Exemplary procedures for preparing tissue cultures of regenerable soybean cells, for example, from soybean cultivar CX414cRR, and regenerating soybean plants therefrom, are disclosed in U.S. Pat. No. 4,992,375; U.S. Pat. No. 5,015,580; U.S. Pat. No. 5,024,944, and U.S. Pat. No. 5,416,011, each of the disclosures of which is specifically incorporated herein by reference in its entirety.

An important ability of a tissue culture is the capability to regenerate fertile plants. This allows, for example, transformation of the tissue culture cells followed by regeneration of transgenic plants. For transformation to be efficient and successful, DNA must be introduced into cells that give rise to plants or germ-line tissue.

Soybeans typically are regenerated via two distinct processes; shoot morphogenesis and somatic embryogenesis (Finer, 1996). Shoot morphogenesis is the process of shoot meristem organization and development. Shoots grow out from a source tissue and are excised and rooted to obtain an intact plant. During somatic embryogenesis, an embryo (similar to the zygotic embryo), containing both shoot and root axes, is formed from somatic plant tissue. An intact plant rather than a rooted shoot results from the germination of the somatic embryo.

Shoot morphogenesis and somatic embryogenesis are different processes and the specific route of regeneration is primarily dependent on the explant source and media used for tissue culture manipulations. While the systems are different, both systems show cultivar-specific responses where some lines are more responsive to tissue culture manipulations than others. A line that is highly responsive in shoot morphogenesis may not generate many somatic embryos. Lines that produce large numbers of embryos during an 'induction' step may not give rise to rapidly-growing proliferative cultures. Therefore, it may be desired to optimize tissue culture conditions for each soybean line. These optimizations may readily be carried out by one of skill in the art of tissue culture through small-scale culture studies. In addition to line-specific responses, proliferative cultures can be observed with both shoot morphogenesis and somatic embryogenesis. Proliferation is beneficial for both systems, as it allows a single, transformed cell to multiply to the point that it will contribute to germ-line tissue.

Shoot morphogenesis was first reported by Wright et al. (1986) as a system whereby shoots were obtained de novo from cotyledonary nodes of soybean seedlings. The shoot meristems were formed subepidermally and morphogenic tissue could proliferate on a medium containing benzyl adenine (BA). This system can be used for transformation if the subepidermal, multicellular origin of the shoots is recognized and proliferative cultures are utilized. The idea is to target tissue that will give rise to new shoots and proliferate those cells within the meristematic tissue to lessen problems associated with chimerism. Formation of chimeras, resulting from transformation of only a single cell in a meristem, are problematic if the transformed cell is not adequately proliferated and does not does not give rise to germ-line tissue. Once the system is well understood and reproduced satisfactorily, it can be used as one target tissue for soybean transformation.

Somatic embryogenesis in soybean was first reported by Christianson et al. (1983) as a system in which embryogenic tissue was initially obtained from the zygotic embryo axis. These embryogenic cultures were proliferative but the repeatability of the system was low and the origin of the embryos was not reported. Later histological studies of a different proliferative embryogenic soybean culture showed that proliferative embryos were of apical or surface origin with a small number of cells contributing to embryo formation. The origin of primary embryos (the first embryos derived from the initial explant) is dependent on the explant tissue and the auxin levels in the induction medium (Hartweck et al., 1988). With proliferative embryonic cultures, single cells or small groups of surface cells of the 'older' somatic embryos form the 'newer' embryos.

Embryogenic cultures can also be used successfully for regeneration, including regeneration of transgenic plants, if the origin of the embryos is recognized and the biological limitations of proliferative embryogenic cultures are understood. Biological limitations include the difficulty in developing proliferative embryogenic cultures and reduced fertility problems (culture-induced variation) associated with plants regenerated from long-term proliferative embryogenic cultures. Some of these problems are accentuated in prolonged cultures. The use of more recently cultured cells may decrease or eliminate such problems.

VI. Genetic Transformation of Soybeans

Genetic transformation may be used to insert a selected transgene into the soybean cultivar of the invention or may, alternatively, be used for the preparation of transgenes which can be introduced into the cultivar of the invention by backcrossing. Methods for the transformation of many economically important plants, including soybeans, are well know to those of skill in the art. Techniques which may be employed for the genetic transformation of soybeans include, but are not limited to, electroporation, microprojectile bombardment, Agrobacterium-mediated transformation and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

Protoplasts may also be employed for electroporation transformation of plants (Bates, 1994; Lazzeri, 1995). For example, the generation of transgenic soybean plants by electroporation of cotyledon-derived protoplasts was described by Dhir and Widholm in Intl. Patent Appl. Publ. No. WO 92/17598, the disclosure of which is specifically incorporated herein by reference.

A particularly efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target soybean cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

Microprojectile bombardment techniques are widely applicable, and may be used to transform virtually any plant species. The application of microprojectile bombardment for the transformation of soybeans is described, for example, in U.S. Pat. No. 5,322,783, the disclosure of which is specifically incorporated herein by reference in its entirety.

Agrobacterium-mediated transfer is another widely applicable system for introducing gene loci into plant cells. An advantage of the technique is that DNA can be introduced into whole plant tissues, thereby bypassing the need for regeneration of an intact plant from a protoplast. Modem Agrobacterium transformation vectors are capable of replication in E. coli as well as Agrobacterium, allowing for convenient manipulations (Klee et al., 1985). Moreover, recent technological advances in vectors for Agrobacterium-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, Agrobacterium containing both armed and disarmed Ti genes can be used for transformation.

In those plant strains where Agrobacterium-mediated transformation is efficient, it is the method of choice because of the facile and defined nature of the gene locus transfer. The use of Agrobacterium-mediated plant integrating vectors to introduce DNA into plant cells is well known in the art (Fraley et al., 1985; U.S. Pat. No. 5,563,055). Use of Agrobacterium in the context of soybean transformation has been described, for example, by Chee and Slightom (1995) and in U.S. Pat. No. 5,569,834, the disclosures of which are specifically incorporated herein by reference in their entirety.

Transformation of plant protoplasts also can be achieved using methods based on calcium phosphate precipitation, polyethylene glycol treatment, electroporation, and combinations of these treatments (see, e.g., Potrykus et al., 1985; Omirulleh et al., 1993; Fromm et al., 1986; Uchimiya et al., 1986; Marcotte et al., 1988). The demonstrated ability to regenerate soybean plants from protoplasts makes each of these techniques applicable to soybean (Dhir et al., 1991).

VII. Definitions

In the description and tables which follow, a number of terms are used. In order to provide a clear and consistent understanding of the specification and claims, including the scope to be given such terms, the following definitions are provided:

A: When used in conjunction with the word "comprising" or other open language in the claims, the words "a" and "an" denote "one or more."

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid ($F_1$), back to one of the parents of the hybrid progeny. Backcrossing can be used to introduce one or more single locus conversions from one genetic background into another.

Brown Stem Rot: This is a visual disease score from 1 to 9 comparing all genotypes in a given test. The score is based on leaf symptoms of yellowing and necrosis caused by brown stem rot. A score of 1 indicates no symptoms. Visual scores range to a score of 9 which indicates severe symptoms of leaf yellowing and necrosis.

Chromatography: A technique wherein a mixture of dissolved substances are bound to a solid support followed by passing a column of fluid across the solid support and varying the composition of the fluid. The components of the mixture are separated by selective elution.

Cross-pollination: Fertilization by the union of two gametes from different plants.

Crossing: The mating of two parent plants.

Diploid: A cell or organism having two sets of chromosomes.

Emasculate: The removal of plant male sex organs or the inactivation of the organs with a cytoplasmic or nuclear genetic factor conferring male sterility or a chemical agent.

Emergence: This is a score indicating the ability of a seed to emerge from the soil after planting. Each genotype is given a 1 to 9 score based on its percent of emergence. A score of 1 indicates an excellent rate and percent of emergence, an intermediate score of 5 indicates average ratings and a 9 score indicates a very poor rate and percent of emergence.

Enzymes: Molecules which can act as catalysts in biological reactions.

$F_1$ Hybrid: The first generation progeny of the cross of two nonisogenic plants.

Genotype: The genetic constitution of a cell or organism.

Haploid: A cell or organism having one set of the two sets of chromosomes in a diploid.

Iron-Deficiency Chlorosis: A plant scoring system ranging from 1 to 9 based on visual observations. A score of 1 means no stunting of the plants or yellowing of the leaves and a score of 9 indicates the plants are dead or dying caused by iron-deficiency chlorosis, a score of 5 means plants have intermediate health with some leaf yellowing.

Linkage: A phenomenon wherein alleles on the same chromosome tend to segregate together more often than expected by chance if their transmission was independent.

Lodging Resistance: Lodging is rated on a scale of 1 to 9. A score of 1 indicates erect plants. A score of 5 indicates plants are leaning at a 45 degree(s) angle in relation to the ground and a score of 9 indicates plants are laying on the ground.

Marker: A readily detectable phenotype, preferably inherited in codominant fashion (both alleles at a locus in a diploid heterozygote are readily detectable), with no environmental variance component, i.e., heritability of 1.

Maturity Date: Plants are considered mature when 95% of the pods have reached their mature color. The maturity date is typically described in measured days from January first, which may be referred to as "Julian Days."

Phenotype: The detectable characteristics of a cell or organism, which characteristics are the manifestation of gene expression.

Phytophthora Tolerance: Tolerance to Phytophthora root rot is rated on a scale of 1 to 9, with a score of 1 being the best or highest tolerance ranging down to a score of 9, which indicates the plants have no tolerance to Phytophthora.

Plant Height: Plant height is taken from the top of soil to the top node of the plant and is measured in inches.

Regeneration: The development of a plant from tissue culture.

Seed Yield (Bushels/Acre): The yield in bushels/acre is the actual yield of the grain at harvest.

Self-pollination: The transfer of pollen from the anther to the stigma of the same plant.

Shattering: The amount of pod dehiscence prior to harvest. Pod dehiscence involves seeds falling from the pods to the soil. This is a visual score from 1 to 9 comparing all genotypes within a given test. A score of 1 means pods have not opened and no seeds have fallen out. A score of 5 indicates approximately 50% of the pods have opened, with seeds falling to the ground and a score of 9 indicates 100% of the pods are opened.

Single Locus Converted (Conversion) Plant: Plants which are developed by a plant breeding technique called backcrossing, wherein essentially all of the desired morphological and physiological characteristics of a soybean cultivar are recovered in addition to the characteristics of the single locus transferred into the cultivar via the backcrossing technique.

Tissue Culture: A composition comprising isolated cells of the same or a different type or a collection of such cells organized into parts of a plant.

Transgene: A genetic locus comprising a sequence which has been introduced into the genome of a soybean plant by transformation.

VIII. Deposit Information

A deposit of the DEKALB Genetics Corporation propriety soybean cultivar CX414cRR, disclosed above and recited in the appended claims, has been made with the American Type Culture Collection (ATCC), 10801 University Blvd., Manassas, Va. 20110-2209. The date of deposit was Nov. 10, 1999. All restrictions upon the deposit have been removed, and the deposit is intended to meet all of the requirements of 37 C.F.R. §1.801–1.809. The accession number for those deposited seeds of soybean cultivar CX414cRR is PTA-933. The deposit will be maintained in the depository for a period of 30 years, or 5 years after the last request, or for the effective life of the patent, whichever is longer, and will be replaced if necessary during that period.

REFERENCES

The following references, to the extent that they provide exemplary procedural or other details supplementary to those set forth herein, are specifically incorporated herein by reference.

Allard, R. W., University of California, Davis, Calif. "Principles of Plant Breeding," Published by John Wiley & Sons, New York, University of California, Davis, Calif., p. 50–98, 1960.

Anderson, W. P., "Weed Science Principles," West Publishing Company, 1983.

Bates, "Genetic transformation of plants by protoplast electroporation," *Mol Biotechnol.,* 2(2):135–145, 1994.

Bernard, R. L., and Cremeens, C. R., "Registration of Williams '82 Soybean" *Crop Sci.,* 28:1027–1028, 1988.

Bernard and Weiss, "Qualitative genetics," *In: Soybeans: Improvement, Production, and Uses,* B. E. Caldwell (Ed.), Am. Soc. of Agron., Madison, Wis., p 117–154, 1973.

Boerma and Moradshahi, "Pollen movement within and between rows to male-sterile soybeans," *Crop Sci.,* 15:858–861, 1975.

Borthwick and Parker, "Photoperiodic perception in Biloxi soybeans," *Bot. Gaz.,* 100:374–387, 1938.

Bowers, G. R., Paschall, E. H., Bernard, R. L.; and Goodman, R. M., "Inheritance of Resistance to Soybean Mosaic Virus in 'Buffalo' and HLS Soybean" Crop science. v. 32 (1) p. 67–72, 1992.

Brim and Stuber, "Application of genetic male sterility to recurrent selection schemes in soybeans," *Crop Sci.,* 13:528–530, 1973.

Carlson, "Morphology", *In: Soybeans: Improvement, Production, and Uses,* B. E. Caldwell (Ed.), Am. Soc. of Agron., Madison, Wis., p 17–95, 1973.

Chee and Slightom, "Transformation of soybean (Glycine max) via *Agrobacterium tumefaciens* and analysis of transformed plants," *Methods Mol. Biol.,* 44:101–119, 1995.

Christianson, Warnick, Carlson, "A morphogenetically competent soybean suspension culture," *Science,* 222:632–634, 1983.

Criswell and Hume, "Variation in sensitivity to photoperiod among early maturing soybean strains," *Crop Sci.,* 12:657–660, 1972.

Dhir, S. K., Dhir S., Sturtevant, A. P., Winholm, J. M., "Regeneration of transformed shoots for electroporated soybean *Glycine max* L. Merr. protoplasts," *Plant Cell Rep* 10(2):97–101, 1991.

Fehr, "Soybean," *In: Hybridization of Crop Plants,* Fehr and Hadley (Eds.), American Society of Agronomy and Crop Science Society of America, Madison, Wis., pp 590–599, 1980.

Fehr, "In: Soybeans: Improvement, Production and Uses," 2nd Edition, *Manograph* 16, p.249, 1987a.

Fehr, W. R., "Principles of Cultivar Development," vol. 1 Theory and Technique and vol. 2 Crop Species, Soybean, Iowa State University, Published by Macmillian Publishing Company, New York, p. 360–376, 1987b.

Finer, Cheng, Verma, "Soybean transformation: Technologies and progress," *In: Soybean: Genetics, Molecular Biology and Biotechnology,* CAB International, Verma and Shoemaker (Ed.), Wallingford, Oxon, UK, pp 250–251, 1996.

Fraley R. T., Rogers S. G., Horsch R. B., Eichholtz D. A., Flick J. S., Fink C. L., Hoffmann N. L., Sanders P. R., "The sev system a new disarmed ti plasmid vector system for plant transformation," *Bio/Technology* 3(7):629–635, 1985.

Fromm M. E., Taylor L. P., Walbot V., "Stable transformation of maize after gene transfer by electroporation," *Nature,* 319(6056):791–793., 1986.

Hamner, "*Glycine max*(L.) Merrill," *In: The Induction of Flowering: Some Case Histories,* L. T. Evans (Ed.), Cornell Univ. Press, Ithaca, N.Y., p 62–89, 1969.

Hartweck, Lazzeri, Cui, Collins, Williams "Auxin orientation effects on somatic embryogenesis from immature soybean cotyledons," *In Vitro Cellular and Develop. Bio.,* 24:821–828, 1988.

Johnson and Bernard, "Soybean genetics and breeding," *In: The Soybean,* A. G. Norman (Ed.), Academic Press, NY, p 1–73, 1963.

Kiihl, Hartwig, Kilen, "Grafting as a tool in soybean breeding," *Crop Sci.,* 17:181–182, 1977.

Klee, Yanofsky, Nester, "Vectors for transformation of higher plants," *Bio-Technology,* 3(7):637–642, 1985.

Kuehl, "Pollen viability and stigma receptivity of *Glycine max* (L.) Merrill," M. S. Thesis, North Carolina State College, Raleigh, N.C., 1961.

Lazzeri, "Stable transformation of barley via direct DNA uptake. Electroporation- and PEG-mediated protoplast transformation," *Methods Mol. Biol.,* 49:95–106, 1995.

Major, Johnson, Tanner, Anderson, "Effects of daylength and temperature on soybean development," *Crop Sci.,* 15:174–179, 1975.

Marcotte W. R., Bayley C. C., Quatrano R. S., "Regulation of a wheat promoter by abscisic acid in rice protoplasts" *Nature,* 335(6189): 454–457, 1988.

Nickell, C. D., and Bernard, R. L., "Registration of L84-5873 and L84-5932 Soybean Germplasm Lines Resistant to Brown Stem Rot," *Crop Sci.* v. 32(3) p. 835, 1992.

Omirulleh, Abraham, Golovkin, Stefanov, Karabaev, Mustardy, Morocz, Dudits, "Activity of a chimeric promoter with the doubled CaMV 35S enhancer element in protoplast-derived cells and transgenic plants in maize," *Plant Mol. Biol.,* 21(3):415–428, 1993.

Parker, Hendricks, Borthwick, Scully, "Action spectrum for the photoperiodic control of floral initiation of short-day plants," *Bot. Gaz.,* 108:1–26, 1946.

Poehlman, J., and Sleper, D. "Breeding Field Crops" Published by the Iowa State University Press, Ames, 1995.

Potrykus I., Paszkowski J., Saul M. W., Petruska J., Shillito R. D., "Molecular and general genetics of a hybrid foreign gene introduced into tobacco by direct gene transfer," *Mol.* Gen. Genet. 199(2):169–177, 1985.

Shanmugasundaram and Tsou, "Photoperiod and critical duration for flower induction in soybean," *Crop Sci.,* 18:598–601, 1978.

Shibles, Anderson, Gibson, "Soybean," *In: Crop Physiology, Some Case Histories,* L. T. Evans (Ed.), Cambridge Univ. Press, Cambridge, England, p 151–189, 1975.

Simmonds, N., "Principles of crop improvement" Published by, Longman, Inc., New York, p. 369–399, 1979.

Sneep, J., and Hendriksen, A., "Plant Breeding Perspectives," Wageningen: Center for Agricultural Publishing and Documentation, 1979.

Sprague and Dudley, eds., *Corn and Improvement,* 3rd ed., 1988.

Uchimiya H., Fushimi T., Hashimoto H., Harada H., Syono K., Sugawara Y., "Expression of a foreign gene in callus derived from DNA-treated protoplasts of Rice (Oryzasativa)" *Mol.* Gen. Genet., 204(2):204–207, 1986.

van Schaik and Probst, "Effects of some environmental factors on flower production and reproductive efficiency in soybeans," *Agron. J,* 50:192–197, 1958.

Walker, Cianzio, Bravo, Fehr, "Comparison of emasculation and nonemasculation for artificial hybridization of soybeans," *Crop Sci.,* 19:285–286, 1979.

Wang et al., "Large-Scale Identification, Mapping, and Genotyping of Single-Nucleotide Polymorphisms in the Human Genome," *Science,* 280:1077–1082, 1998.

Williams et al., "Oligonucleotide Primers of Arbitrary Sequence Amplify DNA Polymorphisms which Are Useful as Genetic Markers," *Nucleic Acids Res.,* 18:6531–6535, 1990.

Wright, Koehler, Hinchee, Carnes, "Plant regeneration by organogenesis in Glycine max," *Plant Cell Reports,* 5:150–154, 1986.

What is claimed is:

1. Soybean seed designated CX414cRR, wherein a sample of said seed has been deposited under accession number PTA-933.

2. A plant produced by growing the seed of claim 1.

3. Pollen of the plant of claim 2.

4. An ovule of the plant of claim 2.

5. A cell of the soybean plant of claim 2.

6. A soybean plant having all of the physiological and morphological characteristics of the plant of claim 2.

7. A tissue culture of regenerable cells of the soybean cultivar CX414cRR, wherein a sample of the seed of said soybean cultivar CX414cRR has been deposited under accession number PTA-933.

8. The tissue culture of claim 7, wherein the regenerable cells are embryos, meristematic cells, pollen, leaves, roots, root tips, flowers or protoplasts or callus derived therefrom.

9. A soybean plant regenerated from the tissue culture of claim 7, wherein the regenerated soybean plant is capable of expressing all the physiological and morphological characteristics of the soybean cultivar CX414cRR, and wherein a sample of the seed of said soybean cultivar CX414cRR has been deposited under accession number PTA-933.

10. The soybean plant of claim 2, further comprising a single locus conversion, wherein said soybean plant is otherwise capable of expressing all the physiological and morphological characteristics of the soybean cultivar CX414cRR, and wherein a sample of the seed of said soybean cultivar CX414cRR has been deposited under accession number PTA-933.

11. The soybean plant of claim 10, wherein the single locus conversion comprises a dominant allele.

12. The soybean plant of claim 10, wherein the single locus conversion comprises a recessive allele.

13. The soybean plant of claim 10, wherein the single locus was stably inserted into a soybean genome by transformation.

14. The soybean plant of claim 13, wherein said single locus comprises a single gene.

15. A first generation ($F_1$) hybrid soybean seed produced by crossing the plant of claim 2 with a second, distinct soybean plant.

16. A first generation $F_1$ hybrid soybean plant produced by growing the seed of claim 15.

17. A method of producing soybean seed, comprising crossing the soybean cultivar CX414cRR with itself or a second soybean plant, wherein a sample of the seed of said soybean cultivar CX414cRR has been deposited under accession number PTA-933.

18. The method of claim 17, further defined as a method of preparing hybrid soybean seed, comprising crossing the soybean cultivar CX414cRR to a second, distinct soybean plant, wherein a sample of the seed of said soybean cultivar CX414cRR has been deposited under accession number PTA-933.

19. The method of claim 18, wherein crossing comprises the steps of:

a) planting seed of soybean cultivar CX414cRR and a second, distinct soybean plant, wherein a sample of the seed of said soybean cultivar CX414cRR has been deposited under accession number PTA-933;

b) growing soybean plants from said seed until said plants bear flowers;

c) cross pollinating a flower of said soybean cultivar CX414cRR with pollen from said second soybean plant or cross pollinating a flower of said second soybean plant with pollen from said soybean cultivar CX414cRR; and d) harvesting seed resulting from said cross pollinating.

* * * * *